US00PP27657P3

(12) United States Plant Patent
Vorsa et al.

(10) Patent No.: US PP27,657 P3
(45) Date of Patent: Feb. 14, 2017

(54) CRANBERRY VARIETY NAMED 'CNJ99-9-96'

(50) Latin Name: ***Vaccinium macrocarpon* Ait.**
Varietal Denomination: CNJ99-9-96

(71) Applicant: Rutgers, The State University of New Jersey, New Brunswick, NJ (US)

(72) Inventors: Nicholi Vorsa, Atco, NJ (US); Jennifer Johnson-Cicalese, Chatsworth, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 151 days.

(21) Appl. No.: 14/544,116

(22) Filed: Nov. 24, 2014

(65) Prior Publication Data

US 2016/0150694 P1 May 26, 2016

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Keith Robinson

(74) *Attorney, Agent, or Firm* — Klarquist Sparkman, LLP; Sheree Lynn Rybak

(57) ABSTRACT

A new cranberry variety distinguished by mid-season ripening, round to ovate fruit, high productivity, and moderate fruit anthocyanin development, as compared to the currently cultivated commercial varieties.

1 Drawing Sheet

Latin name of the genus and species of the plant claimed: *Vaccinium macrocarpon* Ait.

Variety denomination: 'CNJ99-9-96'.

BACKGROUND

The American cranberry (*Vaccinium macrocarpon* Ait.) is a temperate, woody perennial plant species native to North America. The United States is the largest producer, with Wisconsin and Massachusetts representing the majority of cranberry acreage and production, followed by New Jersey, Oregon and Washington. Varieties that currently are commercially cultivated include selections from native populations, and first and second breeding and selection cycle hybrids. Significant acreage is still devoted to varieties that were selected from native cranberry populations from as far back as 1843, including 'Ben Lear' (unpatented), 'Early Black' (unpatented), 'Howes' (unpatented), 'Lemunyon' (unpatented), 'McFarlin' (unpatented) and 'Searles' (unpatented). First breeding and selection hybrid varieties were developed by the United States Department of Agriculture, in cooperation with state Agricultural Experiment Stations in the 1940's, and the program released a series of unpatented varieties in the 1950's including the most widely grown cultivar 'Stevens', which was selected from original test plots in Pemberton, N.J. During the 2000-2010 decade, patented and unpatented varieties from a second breeding and selection cycles have been introduced and grown commercially.

The bulk of cranberry production is for the processed market, including both juice and 'sweetened dried cranberry' (SDC) fruit products, where fruit having specific anthocyanin content (TAcy) ranges are desired. For SDC processors, certain fruit quality criteria are desired, including larger fruit size (>1.5 g/berry), a round fruit shape, mid-range TAcy, moderate to high titratable acidity (TA, 2.3-2.5 citric acid equivalents), and high soluble solids (Brix). Another important cranberry market is fresh fruit, where berry appearance and storage life are essential traits. For economic sustainability, cranberry growers require varieties with consistent high productivity, acceptable levels of disease tolerance to both fruit and vine diseases, and desired season of harvest.

In cranberry, varietal variation for crop productivity is a function of inherent differences among varieties for traits such as stolon vigor, upright (vertical reproductive shoots) density, inflorescence bud production, fruit set and fruit size. Varieties with high stolon vigor will establish more rapidly and reduce the number of years required to achieve maximal production. However, after stolon colonization of the bed, varieties must transition to optimal sexual reproduction mode, and optimal upright density, to achieve high crop production. Cranberry inflorescence bud primordia are set on uprights during the completion of the fruit development period and overwinter in a dormant state, before resuming growth the subsequent spring. Thus, the crop load of a given year, may impact the subsequent year's cropping, contributing to the pronounced biennial bearing habit common to many varieties. Productivity is also subject to environmental effects, e.g., heat and light intensity stresses, cold (frost) stress, water stress (drought and excess), disease, insects, certain pesticides, etc.

TAcy content is a fruit quality component of cranberry, usually having a minimum acceptable value. TAcy is typically measured as mg of total anthocyanin per 100 g fresh weight fruit, using a standard spectrophotometric method (@ 520 nm absorbance). For SDC products, there is a desired range, minimum and maximum, for TAcy, typically 20-40 mg total anthocyanins/100 g fresh weight. Earlier ripening varieties, which typically have higher TAcy, allow for earlier harvest of a crop. Anthocyanins are largely located in the fruit epidermis, which results in a generally larger fruit having lower TAcy.

New Jersey uniquely offers an ideal environment for cranberry breeding because of the climate, soils and water. Of all the cranberry production areas in North America, New Jersey conditions subject the cranberry to the highest disease pressure and heat stresses. The plant and developing fruit must tolerate high heat stress, and fruit and vegetative diseases during the growing season. Over 15 pathogens are known to incite cranberry fruit rot in New Jersey, and the fruit is also subject to heat scald and physiological breakdown. Thus, selection under New Jersey conditions offers the opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as much as possible, the environment of a commercial bed. Breeding plots of 1.5×1.5 m are established with multiple plants and allowed to 'fill in' to form a dense canopy. Two to three years after planting, yield of a given plot is evaluated over a four year minimum to provide for biennial bearing assessment. Parental selection is based on field phenotypic performance, and progeny performance of parental cross combinations based on the objectives of enhancing traits and/or combining the most desirable traits from both parents into one genotype, i.e., variety. Traits evaluated in this cranberry breeding program include yield, ripening season, fruit rot susceptibility/resistance, storage life, scald susceptibility, stolon and upright vigor, total anthocyanin content (TAcy), soluble solids (Brix), titratable acidity, and berry shape and appearance.

SUMMARY

The present disclosure relates to a new and distinctive American cranberry variety, 'CNJ99-9-96', for the processed cranberry market, having a high crop yield potential, a mid-season ripening period, a round to ovate berry. 'CNJ99-9-96' is suited to most areas where cranberry is cultivated. The new disclosed variety 'CNJ99-9-96' resulted from a 1999 cross between the variety 'NJS98-23' (U.S. Plant Pat. No. 18,252) as the seed parent, with the '#35' (unpatented) variety as the pollen parent. '#35' is an unpatented variety from a 'Howes×Searles' cross. '#35' was originally selected from a previous USDA/NJAES cranberry breeding program (Dana MN. Cranberry cultivar list (*Vaccinium macrocarpon*). Fruit Varieties J 37:88-95, 1983).

'CNJ99-9-96' was originally selected from 138 progeny growing in test plots in Chatsworth, N.J. for its very high yield potential, mid-season ripening, large round berry and uniform fruit color. In 2007, 'CNJ99-9-96' was selected for testing in advanced replicated selection trials in Oregon, Washington and Wisconsin. 'CNJ99-9-96' exhibits consistently high yields with mid-season ripening. Although originally selected under New Jersey's environmental stresses, 'CNJ99-9-96' is suited to most cranberry growing areas.

The 'CNJ99-9-96' variety is distinguished from other cranberry varieties in having high yield fruit production with midseason ripening. Fruit are moderate to large with a nearly round shape. 'CNJ99-9-96' can be distinguished from its seed parent 'NJS98-23' by its later bloom, later fruit ripening, and rounder fruit shape; and from its pollen parent '#35' by higher Tacy, earlier bloom, earlier ripening and larger fruit.

'CNJ99-9-96' has been asexually reproduced by cuttings in Chatsworth, N.J. since 2007. Over that period, no evidence of 'off-types' of 'CNJ99-9-96' has been observed. 'CNJ99-9-96' appears genetically stable and reproduces true to type in successive generations of asexual reproduction.

The following description describes the cranberry variety 'CNJ99-9-96'. The original plant and vegetative propagules were observed in a cranberry bed maintained with standard management practices for commercial cranberry production in Chatsworth, Burlington County, N.J. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart (2001).

BRIEF DESCRIPTION OF THE DRAWING

FIG. 1 shows 'CNJ99-9-96' fruit harvested and photographed September 2014 in Chatsworth, N.J.

The colors of an illustration of this type may vary with lighting and other conditions, therefore, color characteristics of this new variety should be determined with reference to the observations described herein, rather than from these illustrations alone.

DETAILED BOTANICAL DESCRIPTION

The following detailed description of the 'CNJ99-9-96' variety is based on observations of plants growing in the field in Chatsworth, N.J. The characteristics of the variety were compared to 'Stevens' and 'Ben Lear' (both unpatented), two widely used cranberry varieties. The observed plantings were 3-6 years of age.

Scientific name: *Vaccinium macrocarpon* Ait.

Parentage:

- *Seed parent*.—The variety 'NJS98-23' (derived from a 'Ben Lear'×'Stevens' cross).
- *Pollen parent*.—The variety '#35' (derived from a 'Howes'×'Searles' cross).

Plant:

- *Vigor*.—General observations of 'CNJ99-9-96' plantings indicate average plant vigor.
- *Growth habit*.—Trailing shrub with very slender stems.
- *Upright length*.—8.1 cm (mean of 30 uprights).
- *Stem diameter*.—1.2 mm at base of current year's growth (mean of 30 stems).
- *Internodes*.—Internode length was 9 mm on 1-year old runners (mean of 15 runners).
- *Productivity*.—In established test plots in Chatsworth, N.J., 'CNJ99-9-96' yields were greater than 'Stevens' and 'Ben Lear'.
- *Hardiness*.—Zones 4-7 (from USDA Misc. Publ. 814).
- *Disease resistance*.—No disease resistance data available for foliar or root pathogens; no unusual propensity to foliar/stem diseases observed.

Leaves: The length, width and other measurements were obtained from observations of 30 typical fully developed leaves in September 2013. Color was determined on actively growing plants.

- *Texture*.—Coriaceous (leathery) on upper and lower surfaces.
- *Length*.—Mean of 9.9 mm, with a maximum 12.2 mm.
- *Width*.—Mean of 3.8 mm, with a maximum width of 5.5 mm.

*Shape*.—Elliptic (2.6:1; length:width).

*Apex shape*.—Rounded.

*Base shape*.—Rounded, nearly sessile.

*Margin*.—Entire, slightly revolute.

*Leaf color*.—Upper leaf surface color ranges from bright green (143C, green group) in new growth to deep green in mature leaves (139A to 137C, green group).

*Pubescence*.—Non-glandular trichomes found along leaf margins towards leaf apex.

Flowers: Observations are from 10 typical flowers collected from test plots in Chatsworth, N.J., Jun. 18, 2014.

*Size and shape*.—Slender, nodding flowers on erect pedicels and in clusters of typically 3-6 flowers; corolla long-conic in bud, petals fully reflexed and divided nearly to the base when open.

*Unopened corolla*.—Approximately 8 mm long and deep pink in color (70D, red-purple group).

*Opened flower*.—Measuring about 10 mm across, 4 petals per flower.

*Petals*.—Narrow and revolute in shape, 8.9 mm by 2.7 mm; pale pink in color (69C, red-purple group); glabrous texture on upper and lower surfaces.

*Pedicel*.—18.4 mm in length by 0.75 mm in diameter with a pubescent texture; color ranges from pale green (195D, greyed green group) to pink (red group 48C).

*Bloom season*.—Bloom typically begins in early June and continues throughout the month. Flowering phenology for 'CNJ99-9-96' is similar to 'Stevens', with peak bloom typically occurring between June 10 and 17 in New Jersey.

*Mean number of flowers per upright*.—4.8 (n=10).

Fruit: Observations are from 30 typical fruit harvested from test plots in Chatsworth, N.J. Sep. 18, 2013 and Oct. 5, 2014.

*Shape*.—Very widely ovate to round (FIG. 1); fruit length:width ratio of 1:1 to 1.2:1; calyx end slightly indented to flat with unpronounced calyx lobes (FIG. 1).

*Size*.—In NJ, average size was 1.77 cm long (pedicel end-calyx end) and 1.7 cm wide.

*Skin*.—Shiny, slight waxy bloom around calyx (FIG. 1), otherwise with slight scattered waxy bloom.

*Color*.—Ranged from 46C (red group) for the lightest berries, 185A (greyed-purple group) for medium berries, to N186C (greyed-purple group) for the darkest (harvested fall 2014).

*Stem pit*.—Small and slightly indented 1.5 mm in diameter.

*Average weight*.—50 berry samples collected from test plots in 2007-2010 had yearly mean berry weights ranging from 1.8 g to 2.4 g, with a maximum berry weight of 3.2 g.

*Fruit firmness*.—Very firm.

*Number of seeds*.—Mean seed number per fruit was 16; with a maximum of 45 seeds/fruit observed.

Seeds: Observations are from 10 seeds extracted from typical fruit harvested from test plots in Chatsworth, N.J., October 2015.

*Size*.—2.2 mm in length by 1.3 mm in width.

*Shape*.—An oval that is slightly triangular and with elongated pointed ends.

*Color*.—165b (greyed orange group, R.H.S.).

*Texture*.—Striated.

*Fruit chemistry*.—100 g samples of fruit were harvested each year from test plots in Chatsworth, N.J. and evaluated for fruit chemistry. TAcy in early-mid September 'CNJ99-9-96' (12 mg/100 g FW), is less than 'Ben Lear' (24 mg/100 g FW) and greater than 'Stevens' (5 mg/100 g FW). 'CNJ99-9-96' had titratable acidity values ranging from 2.0% to 2.6%, and Brix values of 7.5% mid-Sept to 9.0% late-Sept-Oct.

*Fruit production*.—'CNJ99-9-96' season is mid-season, ripening after early varieties (e.g., 'Ben Lear', 'NJS98-23'), and before later season varieties ('Stevens' and 'CNJ97-105-4'; U.S. Plant Pat. No. 19,434).

*Usage*.—Most suitable for processed cranberry products and fresh fruit.

*Disease resistance*.—In New Jersey, where disease pressure is severe, and in Wisconsin, 'CNJ99-9-96' typically has less fruit rot (a disease complex of over 15 pathogens, primarily *Colletotrichum gloeosporioides, Physalospora vaccinii, Phyllosticta vaccinii, Phomopsis vaccinii,* and *Coleophoma empetri*) than 'Stevens'.

We claim:

1. A new and distinct variety of cranberry plant, substantially as herein shown and described.

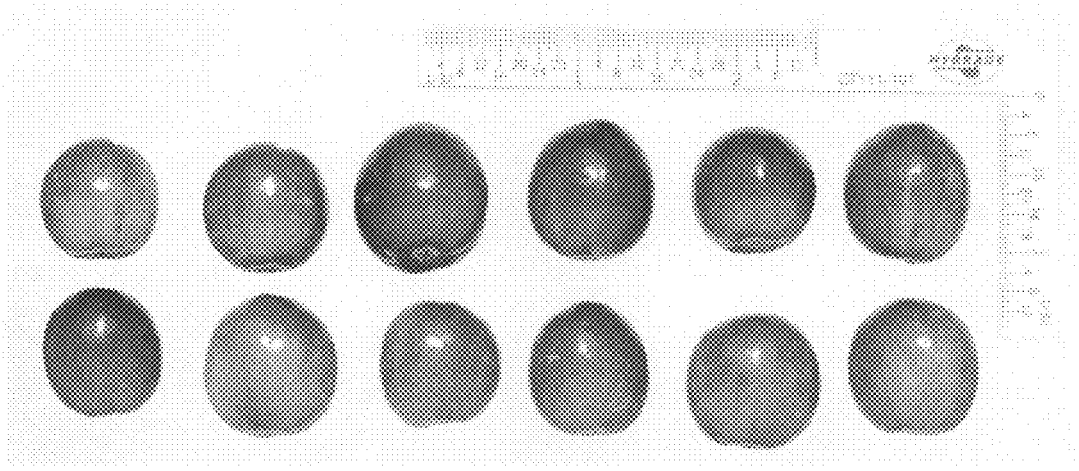

* * * * *